United States Patent
Thompson et al.

(10) Patent No.: US 10,219,373 B2
(45) Date of Patent: Feb. 26, 2019

(54) SELECTIVE DEPOSITION OF THIN FILM DIELECTRICS USING SURFACE BLOCKING CHEMISTRY

(71) Applicant: Applied Materials, Inc., Santa Clara, CA (US)

(72) Inventors: David Thompson, San Jose, CA (US); Mark Saly, Santa Clara, CA (US); Bhaskar Jyoti Bhuyan, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/912,388

(22) Filed: Mar. 5, 2018

(65) Prior Publication Data

US 2018/0199432 A1    Jul. 12, 2018

Related U.S. Application Data (63) Continuation of application No. 15/142,497, filed on Apr. 29, 2016, now Pat. No. 9,911,591.

(Continued)

(51) Int. Cl.
*H01L 21/02* (2006.01)
*H05K 1/02* (2006.01)
(Continued)

(52) U.S. Cl.
CPC ............ *H05K 1/0296* (2013.01); *C07F 7/00* (2013.01); *C23C 16/04* (2013.01); *C23C 16/455* (2013.01); *C23C 16/45525* (2013.01); *C23C 16/50* (2013.01); *G03G 15/50* (2013.01); *G03G 15/80* (2013.01); *G03G 21/1652* (2013.01); *H01L 21/0217* (2013.01); *H01L 21/0228* (2013.01); *H01L 21/02211* (2013.01); *H01L 21/02307* (2013.01); *H01L 21/3105* (2013.01); *H01L 21/31133* (2013.01); *H01L 21/32* (2013.01); *H01L 21/67207* (2013.01); *H05K 1/0269* (2013.01); *H05K 1/117* (2013.01); *H05K 3/403* (2013.01); *H05K 3/4015* (2013.01); *H05K 2201/0394* (2013.01); *H05K 2201/09063* (2013.01); *H05K 2201/09181* (2013.01);

(Continued)

(58) Field of Classification Search
CPC ......... H01L 21/02; H01L 21/31; H01L 21/44; G03F 1/00; G01N 21/55; G01N 30/00
USPC ................ 174/268; 422/88; 423/22; 424/63; 438/240, 680, 778
See application file for complete search history.

(56) References Cited

U.S. PATENT DOCUMENTS 6,077,643 A    6/2000   Kumar et al.
6,200,893 B1   3/2001   Sneh
(Continued)

OTHER PUBLICATIONS

PCT International Preliminary Report on Patentability in PCT/US2016/030057 dated Nov. 16, 2017, 7 pages.

(Continued)

*Primary Examiner* — Xiaoliang Chen
(74) *Attorney, Agent, or Firm* — Servilla Whitney LLC (57) ABSTRACT

Methods of depositing a film selectively onto a first substrate surface relative to a second substrate surface. Methods include soaking a substrate surface comprising hydroxyl-terminations with a silylamine to form silyl ether-terminations and depositing a film onto a surface other than the silyl ether-terminated surface.

20 Claims, 2 Drawing Sheets

Related U.S. Application Data (60) Provisional application No. 62/155,529, filed on May 1, 2015.

(51) Int. Cl.

| | |
|---|---|
| *C23C 16/455* | (2006.01) |
| *C23C 16/04* | (2006.01) |
| *C23C 16/50* | (2006.01) |
| *H01L 21/311* | (2006.01) |
| *H01L 21/67* | (2006.01) |
| *C07F 7/00* | (2006.01) |
| *H01L 21/3105* | (2006.01) |
| *H01L 21/32* | (2006.01) |
| *G03G 15/00* | (2006.01) |
| *G03G 21/16* | (2006.01) |
| *H05K 1/11* | (2006.01) |
| *H05K 3/40* | (2006.01) |

(52) U.S. Cl.
CPC ............. *H05K 2201/10287* (2013.01); *H05K 2201/10363* (2013.01)

(56) References Cited

U.S. PATENT DOCUMENTS

| | | |
|---|---|---|
| 8,728,955 B2 | 5/2014 | Lavoie et al. |
| 2002/0115252 A1* | 8/2002 | Haukka .................. C23C 16/40 438/240 |
| 2003/0083189 A1 | 5/2003 | Yamamoto et al. |
| 2005/0208760 A1 | 9/2005 | Ryan |
| 2005/0277294 A1* | 12/2005 | Schaeffer ............ C23C 16/0272 438/680 |
| 2006/0199399 A1 | 9/2006 | Muscat |
| 2007/0196297 A1* | 8/2007 | Ruckenstein ........... C01B 33/02 424/63 |
| 2009/0061327 A1* | 3/2009 | Sengupta ............... B82Y 10/00 430/5 |
| 2009/0141376 A1* | 6/2009 | Smith .................. G01N 21/553 359/833 |
| 2010/0248473 A1 | 9/2010 | Ishizaka et al. |
| 2011/0116974 A1* | 5/2011 | Serban ................ G01N 29/022 422/88 |
| 2011/0198736 A1 | 8/2011 | Shero et al. |
| 2011/0308603 A1* | 12/2011 | Vermang .......... H01L 31/02167 136/256 |
| 2012/0196451 A1 | 8/2012 | Mallick |
| 2012/0213940 A1 | 8/2012 | Mallick |
| 2015/0147824 A1 | 5/2015 | Cameron et al. |
| 2015/0299848 A1 | 10/2015 | Haukka et al. |
| 2016/0222504 A1 | 8/2016 | Haukka et al. |

OTHER PUBLICATIONS

PCT International Search Report and Written Opinion in PCT/US2016/030057 dated Sep. 12, 2016, 11 pages.

Bitto, Florian , et al., "Chlorosilanes and 3,5-Dimethylpyrazole: Multinuclear Complexes, Acetonitrile Insertion and 29Si NMR Chemical-Shift Anisotropy Studies", Eur. J. Inorg. Chem. 2013, 2954-2962.

Mahé, Olivier , et al., "Deoxofluorination Reactions Using N,N-Disubstituted Aminodifluorosulfinium Tetrafluoroborate Salts", Journal of Fluorine Chemistry 153 (2013) 57-60.

Smith, Catherine J., et al., "Palladium catalysed aryl amination reactions in supercritical carbon dioxide", Org. Biomol. Chem., 2005, 3, 3767-3781.

* cited by examiner

SELECTIVE DEPOSITION OF THIN FILM DIELECTRICS USING SURFACE BLOCKING CHEMISTRY

CROSS-REFERENCE TO RELATED APPLICATIONS

This application is a continuation of U.S. patent application Ser. No. 15/142,497, filed Apr. 29, 2016, which claims priority to U.S. Provisional Application No. 62/155,529, filed May 1, 2015, the entire disclosures of which are hereby incorporated by reference herein.

FIELD

Embodiments of the disclosure generally relate to methods of selectively depositing a film. More particularly, embodiments of the disclosure are directed to methods of selectively depositing a film using alcohol selective reduction and selective protection.

BACKGROUND

Selective deposition processes are gaining a lot of momentum mostly because of the need for patterning applications for semiconductors. Traditionally, patterning in the microelectronics industry has been accomplished using various lithography and etch processes. However, since lithography is becoming exponentially complex and expensive the use of selective deposition to deposit features is becoming much more attractive. Another potential application for selective deposition is gap fill. In gap fill, the fill film is grown selectively from the bottom of a trench towards the top. Selective deposition could be used for other applications such as selective sidewall deposition where films are grown on the side of the fin. This would enable the deposition of a sidewall spacer without the need for complex patterning steps.

Therefore, there is a need in the art for methods of selectively depositing a film onto one surface selectively over a different surface.

SUMMARY

One or more embodiments of the disclosure are directed to methods of depositing a film. A substrate comprising a first substrate surface including hydroxyl-terminated surface and a second substrate surface including a hydrogen-terminated surface is provided. The substrate is exposed to a silylamide to react with the hydroxyl-terminated surface to form a silyl ether-terminated surface. The substrate is exposed to one or more deposition gases to deposit a film on second substrate surface selectively over the silyl ether-terminated surface.

Additional embodiments of the disclosure are directed to methods of depositing a film. A substrate comprising a first substrate surface including a hydroxyl-terminated surface and a second substrate surface including a hydrogen-terminated dielectric is provided. The substrate is soaked with a silylamide to react with the hydroxyl-terminated surface to form a silyl ether-terminated surface. The substrate is exposed to one or more deposition gases to deposit a silicon nitride film on the second substrate surface selectively over the first substrate surface.

Further embodiments of the disclosure are directed to methods of depositing a film. A substrate comprising a first substrate surface including a hydroxyl-terminated surface and a second substrate surface including a hydrogen-terminated dielectric is provided. The substrate is soaked with a silylamide comprising one or more of 1-trimethylsilylpyrrolidine, 1-trimethylsilylpyrrole and/or 3,5-dimethyl-1-trimethylsilylpyrazole to react with the hydroxyl-terminated surface to form a silyl ether-terminated surface. The substrate is exposed to one or more deposition gases to deposit a silicon nitride film on the second substrate surface selectively over the first substrate surface.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

There are a variety of methods that could be used for selective depositions. Embodiments of the disclosure are directed to methods that employ surface deactivation by taking advantage of the surface chemistry of two different surfaces. Since two different surfaces will have different reactive handles, the differences can be taken advantage of by utilizing molecules that will react with one surface (to deactivate that surface) and not react with the other surface. Some embodiments of the disclosure use trimethylsilylamide chemistry to react with Si—OH groups of one surface and not react with Si—H terminated second surface.

As used in this specification and the appended claims, the term "substrate" and "wafer" are used interchangeably, both referring to a surface, or portion of a surface, upon which a process acts. It will also be understood by those skilled in the art that reference to a substrate can also refer to only a portion of the substrate, unless the context clearly indicates otherwise. Additionally, reference to depositing on a substrate can mean both a bare substrate and a substrate with one or more films or features deposited or formed thereon.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, silicon nitride, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal and/or bake the substrate surface. In addition to film processing directly on the surface of the substrate itself, in the present disclosure, any of the film processing steps disclosed may also be performed on an underlayer formed on the substrate as disclosed in more detail below, and the term "substrate surface" is intended to include such underlayer as the context indicates. Thus for example, where a film/layer or partial film/layer has been deposited onto a substrate surface, the exposed surface of the newly deposited film/layer becomes the substrate surface. What a given substrate surface comprises will depend on what films are to be deposited, as well as the particular chemistry used. In one or more embodiments, the first substrate surface will comprise a metal, and the second substrate surface will comprise a dielectric, or vice versa. In some embodiments, a substrate surface may comprise certain functionality (e.g., —OH, —NH, etc.).

Likewise, the films that can be used in the methods described herein are quite varied. In some embodiments, the films may comprise, or consist essentially of a metal. Examples of metal films include, but are not limited to, cobalt (Co), copper (Cu), nickel (Ni), tungsten (W), etc. In some embodiments, the film comprises a dielectric. Examples include, $SiO_2$, SiN, $HfO_2$, etc.

As used in this specification and the appended claims, the terms "reactive gas", "precursor", "reactant", and the like, are used interchangeably to mean a gas that includes a species which is reactive with a substrate surface. For example, a first "reactive gas" may simply adsorb onto the surface of a substrate and be available for further chemical reaction with a second reactive gas.

Embodiments of the disclosure provide methods of selectively depositing a metal film onto one surface over a second surface. As used in this specification and the appended claims, the term "selectively depositing a film on one surface over another surface", and the like, means that a first amount of the film is deposited on the first surface and a second amount of film is deposited on the second surface, where the second amount of film is less than the first amount of film or none. The term "over" used in this regard does not imply a physical orientation of one surface on top of another surface, rather a relationship of the thermodynamic or kinetic properties of the chemical reaction with one surface relative to the other surface. For example, selectively depositing a cobalt film onto a copper surface over a dielectric surface means that the cobalt film deposits on the copper surface and less or no cobalt film deposits on the dielectric surface; or that the formation of the cobalt film on the copper surface is thermodynamically or kinetically favorable relative to the formation of a cobalt film on the dielectric surface.

Figure 1:
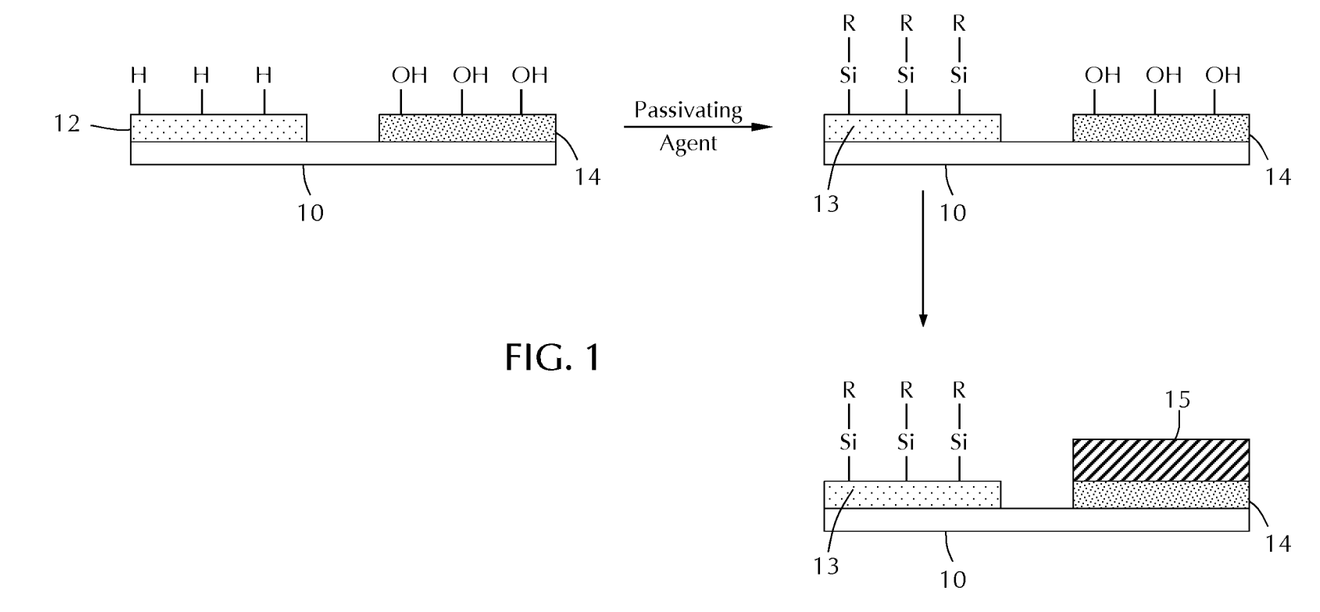
FIG. 1 shows a schematic representation of a processing method in accordance with one or more embodiment of the disclosure.

With reference to FIG. 1, one or more embodiments of the disclosure are directed to methods of depositing a film. A substrate 10 comprising a first substrate surface 12 and a second substrate surface 14 is provided. The first substrate surface 12 includes a hydroxyl-terminated surface (i.e., a surface having —OH groups). The second substrate surface 14 includes a hydrogen-terminated surface (i.e., a surface having —H terminations, e.g., Si—H or Si—$NH_2$). A hydrogen-terminated surface can include an amine terminated surface (as might be found in a SiN film). In some embodiments, the first substrate surface 12 comprises substantially only hydroxyl-terminations. As used in this regard, the term "substantially only" means that the surface terminations of the first substrate surface are at least about 75%, 80%, 85%, 90% or 95% hydroxyl terminations. In some embodiments, the second substrate surface 14 comprises substantially only hydrogen terminations. As used in this regard, the term "substantially only" means that the surface terminations of the second substrate surface are at least about 75%, 80%, 85%, 90% or 95% hydrogen terminations. In some embodiments, one or more of the first substrate surface 12 and the second substrate surface 14 comprises a dielectric. In one or more embodiments, the first substrate surface 12 comprises a dielectric. The dielectric can be a low-k dielectric or a high-k dielectric.

The substrate 10 is exposed to a silylamide to react with one or more of the first substrate surface 12 and/or the second substrate surface 14. Exposing the substrate surface to the silylamide can be done by any suitable process. Exposure may be referred to as soaking, in which at least some of the substrate surfaces are "soaked" or "flooded" with the silylamide to allow surface reactions to occur. As used in this specification and the appended claims, the term "silylamide" refers to a compound have a silicon-nitrogen bond in which the nitrogen is part of an amine group or part of a heterocyclic ring. FIG. 1 shows a schematic of the initial surface reactions that occur on a Si—OH terminated surface (the first substrate surface 12) versus a Si—H terminated surface (the second substrate surface 14).

Silicon-carbon bonds are very strong and not very reactive. Without being bound by any particular theory of operation, it is believed that a silylamide can deactivate any surfaces by the silicon-carbon bond. Silicon-carbon bonds are also thermally stable, showing stability up to 600° C. Silylamide groups are not reactive towards the basic Si—H group and will not deactivate surfaces terminated with Si—H. It has been found that use of a silylamide can allow for selectively depositing certain dielectric processes on Si—H and not on Si—OH terminated surfaces.

The silylamide in FIG. 1 is denoted by $(CH_3)_3$Si-L in which L is any amine or heterocyclic amine. The silylamide shown in FIG. 1 is merely indicative of one possible silylamide and should not be taken as limiting the scope of the disclosure. The silylamide reacts with the hydroxyl-terminations on the first substrate surface 12 to form a silyl ether-terminated surface 13 and evolve HL. As used in this specification and the appended claims, the term "silyl ether" refers to a compound having a Si—O bond that forms a surface termination.

Suitable silyamides are those that can react with the surface hydroxyl groups to form a silyl ether terminated surface. In some embodiments, the silylamide comprises an organic silylamide. As used in this specification and the appended claims, the term "organic silylamide" refers to a compound in which the silicon atom is bonded to one or more organic groups. For example, as shown in FIG. 1, the organic silylamide is a trimethylsilyl amide.

In one or more embodiments, the organic silylamide comprises a silicon atom bonded substantially only to carbon and/or nitrogen atoms. As used in this specification and the appended claims, the term "substantially only to carbon and/or nitrogen" means that there is less than about 5% of the silicon atoms are bonded to atoms other than carbon or nitrogen, on an atomic basis. In one or more embodiments, the organic silylamide comprises substantially no Si—H or Si—OH bonds. As used in this specification and the appended claims, the term "substantially no Si—H and/or Si—OH bonds" means that there is less than about 5% of the silicon atoms are bonded to hydrogen or hydroxides.

In some embodiments, the organic silylamide comprises one or more of trimethylsilylamide, triethylsilylamide, ethyldimethylsilylamide and/or diethylmethylsilylamide. In one or more embodiments, the silylamide includes an amide comprising one or more of pyrrolidine, pyrrole, pyrazole, dimethylamine, diethylamine, ethylmethylamine, cyclic secondary amine, saturated cyclic amine and/or unsaturated cyclic amine.

Trimethylsilylamides contain a basic amine group which will readily react with Si—OH groups to form the free amine and result in the formation of a very stable (CH3)3Si—O—Si moiety. In certain embodiments, the silylamide comprises one or more of 1-trimethylsilylpyrrolidine, 1-trimethylsilylpyrrole and/or 3,5-dimethyl-1-trimethylsilylpyrazole.

The temperature at which the pre-treatment (i.e., the silylamide) is exposed to the substrate surfaces depends on, for example, the first surface, the second surface, the silylamide, planned future processing, past processing and the processing equipment being used. For example, a lower temperature process may help preserve the thermal budget of the substrate for further processing. In some embodiments, the substrate surfaces are exposed to the silylamide at a temperature in the range of about 50° C. to about 600° C.

The silylamide exposure time can vary depending on, for example, the reactivity of the silylamide toward the subject surface materials. In some embodiments, the substrate is exposed to the silylamide for a time in the range of about 10 seconds to about 60 minutes. In some embodiments, the silylamide exposure occurs for a time less than about 10 minutes, 5 minutes, 1 minute or 0.5 minutes.

After formation of the silyl-ether terminated surface 13, a film can be deposited onto the second substrate surface 14 without affecting the silyl-ether terminated surface 13. The film can be deposited by any suitable technique. In some embodiments, the substrate 10 is exposed to one or more deposition gases to deposit a film 15 on the second substrate surface 14 selectively versus the silyl-ether terminated surface 13. In one or more embodiments, the deposited film 15 comprises SiN. The film 15 of some embodiments is deposited by atomic layer deposition comprising sequential exposure to a silicon-containing gas and a nitrogen-containing gas. Suitable silicon-containing gases include, but are not limited to silane, disilane, trisilane, monochlorosilane, dichlorosilane, trichlorosilane, silicon tetrachloride, hexachlorodisilane (HCDS), a halogenated carbosilane and combinations thereof. Suitable nitrogen-containing gases include, but are not limited to, nitrogen-containing plasma, ammonia, an amine, hydrazine and/or carbonitride.

The film formation process can be CVD process in which the first reactive gas and the second reactive gas are exposed to the substrate surface at the same time so that the first reactive gas and the second reactive gas mix during formation of the film.

In some embodiments, the film formation process is an ALD process in which the substrate, or portion of the substrate, is sequentially exposed to the first reactive gas and the second reactive gas. Sequential exposure means that the substrate, or portion of the substrate, is exposed to only one of the first reactive gas and the second reactive gas at any given time. In ALD processes there is substantially no gas phase mixing of the first reactive gas and the second reactive gas.

Figure 2:
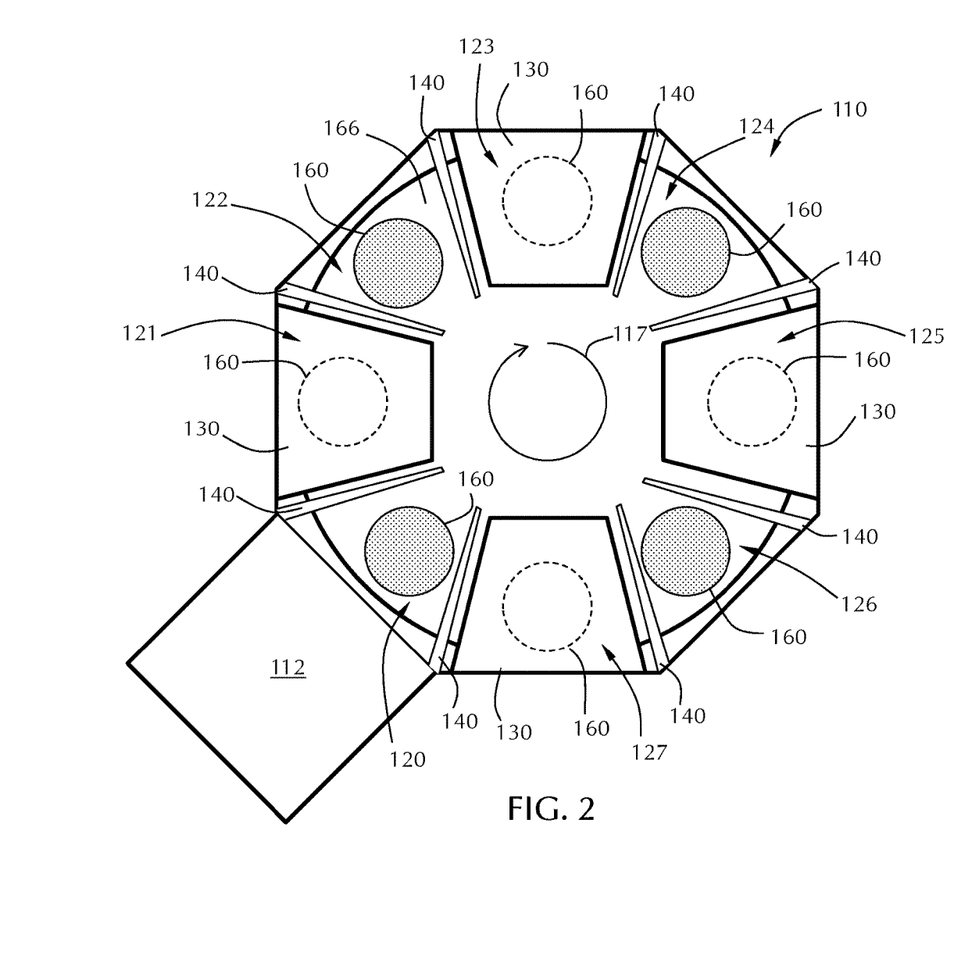
FIG. 2 shows an embodiment of a batch processing chamber in accordance with one or more embodiment of the disclosure.

FIG. 2 shows an embodiment of a spatial atomic layer deposition batch processor, referred to as a processing chamber 110. The shape of the processing chamber 110 and the components described are merely exemplary and should not be taken as limiting the scope of the disclosure. For example the octagonal shaped processing chamber can be circular or hexagonal, etc. A load lock 112 chamber is connected to a front (which may be arbitrarily designated as the front) of the processing chamber 110 and provides a way of isolating the interior of the processing chamber from the atmosphere outside of the processing chamber 110. Load lock 112 can be any suitable load lock, and can operate in the manner as any suitable load lock, as is known to those skilled in the art.

A substrate 160 passes into the processing chamber 110 into a loading region 120. In the loading region 120, the substrate 160 can be subjected to processing conditions or can rest. Processing conditions in the loading region can be, for example, pre-heating of the substrate 160 to process temperature, exposure to a pre-treatment (e.g., silylamine exposure) or cleaning. In some embodiments, the substrate 160 is exposed to a pre-treatment comprising a gaseous silylamine.

The substrate 160 is moved laterally from the loading region through a gas curtain 140 to a first process region 121. The use of ordinal numbers to describe the process regions is merely exemplary and should not be taken as limiting the scope of the disclosure. Use of the terms "first process region", "second process region", etc., are merely intended as a convenient way of describing different portions of the processing chamber. The specific location of the process regions within the chamber is not limited to the embodiment shown. Lateral movement of the substrate 160 can occur by rotation of a susceptor 166 about an axis indicated by arrow 117, or in the opposite direction of arrow 117. In the first process region 121, the substrate 160 may be exposed a first reactive gas or precursor for an ALD process.

The substrate 160 is moved laterally within the processing chamber 110 from the first process region 121 through a gas curtain 140 to a second process region 122. The gas curtains 140 provide separation between the various process regions within the processing chamber 110. The gas curtains are shown as a wedge shaped component with a truncated inner end but it will be understood that the gas curtain can be any shape suitable for maintaining isolation of the process regions. The gas curtain 140 can include any suitable combination of inert gases and/or vacuum ports that are capable of separating the atmospheres of the individual process regions. In some embodiments, the gas curtains 140 comprise, in order, a vacuum port, an inert gas port and another vacuum port. At some point during movement of the substrate from the first process region 121 to the second process region 122, one portion of the substrate is exposed to the second process region while another portion of the substrate is exposed to the first process region 121 and a center portion is within the gas curtain 140.

Once in the second process region 122, the substrate 160 might be exposed to a second reactive gas that can complete the ALD process. For example, if a SiN film is being formed, the first reactive gas might be a silicon-containing precursor and the second reactive gas might be a nitrogen-containing gas.

The substrate 160 can be continuously laterally moved along the circular path indicated by arrow 117 to expose the substrate to the third process region 123, fourth process region 124, fifth process region 125, sixth process region 126 and the seventh process region 127 and back to the loading region. In some embodiments, the loading region 120, second process region 122, fourth process region 124 and sixth process region 126 each expose the substrate to the second reactive gas comprising an alcohol and the first process region 121, third process region 123, fifth process region 125 and seventh process region 127 each expose the substrate 160 to the first reactive gas. The embodiment shown in FIG. 2 has a wedge shaped gas distribution assembly 130 positioned over the first, third, fifth and seventh process regions for clarity to show the substrate 160 on the susceptor 166 between gas distribution assemblies 130. However, it will be understood that any or all of the process regions can have a gas distribution assembly 130 or other gas delivery system.

Once the film 15 has been deposited, further processing may be performed. For example, de-protection of the first substrate surface 12 may occur to remove the silyl-ether terminations. This can be done by any suitable method or technique that can remove the silyl-ether terminations from the surface after depositing the film 15. The further processing can be performed in the same processing chamber or a different processing chamber.

In some embodiments, the silylamine exposure is followed by ALD deposition cycles. At some intervals, the silyl ether is etched and a new silyl ether layer is formed. In some embodiments, the silyl ether is etched after no more than about 300 ALD cycles, or 200 ALD cycles, or 100 ALD cycles, or 75 ALD cycles or 50 ALD cycles. In one or more embodiments, the etch process is performed after every 100 ALD deposition cycles, followed by treatment with the silylamine again prior to continuing deposition.

In some embodiments, the process occurs in a batch processing chamber. For example, in a rotating platen chamber, in which one or more wafers are placed on a rotating holder ("platen"). As the platen rotates, the wafers move between various processing areas. For example, in ALD, the processing areas would expose the wafer to precursor and reactants. In addition, plasma exposure may be useful to properly treat the film or the surface for enhanced film growth, or to obtain desirable film properties.

Some embodiments of the disclosure process a substrate with the first surface and the second surface in a single processing chamber where in a first portion of the chamber, the substrate surfaces are exposed to the silylamine. The substrate may then be rotated to a second portion of the processing chamber, and/or subsequent portion of the processing chamber to deposit a film. In some embodiments, the substrate can be further rotated or moved to another portion of the processing chamber where the silyl ether-terminations can be removed. To separate each or any of the portions, or regions, of the processing chamber, a gas curtain can be employed. The gas curtain provides one or more of purge gas and vacuum ports between the processing regions to prevent reactive gases from moving from one region to an adjacent region. In some embodiments, the substrate is exposed to more than one processing region at the same time, with one portion of the substrate in a first region (e.g., for silylamine exposure) and another portion of the substrate at the same time being in a separate region of the processing chamber.

Embodiments of the disclosure can be used with either a linear processing system or a rotational processing system. In a linear processing system, the width of the area that the plasma exits the housing is substantially the same across the entire length of front face. In a rotational processing system, the housing may be generally "pie-shaped" or "wedge-shaped". In a wedge-shaped segment, the width of the area that the plasma exits the housing changes to conform to a pie shape. As used in this specification and the appended claims, the terms "pie-shaped" and "wedge-shaped" are used interchangeably to describe a body that is a generally circular sector. For example, a wedge-shaped segment may be a fraction of a circle or disc-shaped object and may have a truncated point. The inner edge of the pie-shaped segment can come to a point or can be truncated to a flat edge or rounded. The path of the substrates can be perpendicular to the gas ports. In some embodiments, each of the gas injector assemblies comprises a plurality of elongate gas ports which extend in a direction substantially perpendicular to the path traversed by a substrate. As used in this specification and the appended claims, the term "substantially perpendicular" means that the general direction of movement of the substrates is along a plane approximately perpendicular (e.g., about 45° to 90°) to the axis of the gas ports. For a wedge-shaped gas port, the axis of the gas port can be considered to be a line defined as the mid-point of the width of the port extending along the length of the port.

Additional embodiments of the disclosure are directed to methods of processing a plurality of substrates. The plurality of substrates is loaded onto substrate support in a processing chamber. The substrate support is rotated to pass each of the plurality of substrates across a gas distribution assembly to expose the substrate surface to the silylamine, deposit a film on the substrate and, optionally, remove the silyl ether layer.

Rotation of the carousel can be continuous or discontinuous. In continuous processing, the wafers are constantly rotating so that they are exposed to each of the injectors in turn. In discontinuous processing, the wafers can be moved to the injector region and stopped, and then to the region between the injectors and stopped. For example, the carousel can rotate so that the wafers move from an inter-injector region across the injector (or stop adjacent the injector) and on to the next inter-injector region where the carousel can pause again. Pausing between the injectors may provide time for additional processing between each layer deposition (e.g., exposure to plasma). The frequency of the plasma may be tuned depending on the specific reactive species being used. Suitable frequencies include, but are not limited to, 400 kHz, 2 MHz, 13.56 MHz, 27 MHz, 40 MHz, 60 MHz and 100 MHz.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or the substrate can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system", and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. The details of one such staged-vacuum substrate processing apparatus are disclosed in U.S. Pat. No. 5,186,718, entitled "Staged-Vacuum Wafer Processing Apparatus and Method," Tepman et al., issued on Feb. 16, 1993. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants after forming the layer on the surface of the substrate. According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

During processing, the substrate can be heated or cooled. Such heating or cooling can be accomplished by any suitable means including, but not limited to, changing the temperature of the substrate support (e.g., susceptor) and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discreet steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

Trimethylsilylamide Preparation

One way to prepare the trimethylsilylamide compound is by salt metathesis by treating lithium amide with trimethylsilylchloride. The reaction scheme is shown in Equation 1, where L can be equal to any amine or heterocyclic amine. Some specific examples of amines are dimethylamine, diethylamine, pyrollidine, pyrazole and pyrrole.

Synthesis of 1-trimethylsilylpyrrolidine

Equation 2 shows the synthetic scheme for 1-trimethylsilylpyrrolidine, referred to as BL1. 6.5 mL (80 mmol) of pyrrolidine was dissolved in 250 mL hexane and the solution was cooled down to −78° C. To this solution, 50 mL (80 mmol) of 1.6 M n-butyl lithium in hexane was added drop wise over a period of 15 min. The resultant reaction mixture was allowed to reach room temperature slowly and stirred for 30 min. The reaction mixture was then again cooled to −78° C. and a 20 mL hexane solution containing 10.1 mL (80 mmol) trimethylsilyl chloride was added over a period of 10 min. The reaction mixture was allowed to reach room temperature slowly and stirred for 12 h. The white precipitate was filtered under an inert atmosphere and hexane was evaporated under vacuum. The product was distilled as a colorless liquid at 110° C. @ 760 torr. Yield: 8.9 g (77.5%). $^1$HNMR (400.18 MHz, $C_6D_6$) 2.87 (m, 4H), 1.57 (m, 4H), 0.11 (s, 9H) ppm; $^{13}$CNMR (100.64 MHz, $C_6D_6$) 1.08 ppm.

Synthesis of 1-trimethylsilylpyrrole

Equation 3 shows a synthetic scheme for 1-trimethylsilylpyrrole, also referred to as BL2. First, 5.55 mL (80 mmol) of pyrrole was dissolved in 250 mL hexane and the solution was cooled down to −78° C. To the solution, 50 mL (80 mmol) of 1.6 M n-butyl lithium in hexane was added drop wise over a period of 15 min. The resultant reaction mixture was allowed to attain room temperature slowly and stirred for 30 min. The reaction mixture was then again cooled to −78° C. and a 20 mL hexane solution of 10.1 mL (80 mmol) trimethylsilyl chloride was added over a period of 10 min. The reaction mixture was allowed to attain room temperature slowly and stirred for 12 h. The white precipitate was filtered under inert atmosphere and hexane was evaporated under vacuum. The product was distilled as a colorless liquid at 130° C. @ 760 torr. Yield: 8.7 g (78.2%). $^1$HNMR (400.18 MHz, $C_6D_6$) 6.74 (s, 2H), 6.54 (s, 2H), 0.07 (s, 9H) ppm; $^{13}$CNMR (100.64 MHz, $C_6D_6$) 123.47, 112.20, −0.01 ppm. Mass spectrometry: m/Z calc for [M+H]$^+$=140.1, found 140.2.

-continued

BL2

Synthesis of 3,5-dimethyl-1-trimethylsilylpyrazole

Equation 4 shows a synthetic scheme for 3,5-dimethyl-1-trimethylsilylpyrazole, also referred to as BL3. 7.7 g (80 mmol) of 3,5-dimethyl pyrazole was dissolved in 250 mL hexane and the solution was cooled down to −78° C. To this solution, 50 mL (80 mmol) of 1.6 M n-butyl lithium in hexane was added drop wise over a period of 15 min. Resultant reaction mixture was allowed to attain room temperature slowly and stirred for 30 min. The reaction mixture was then again cooled to −78° C. and a 20 mL hexane solution of 10.1 mL (80 mmol) trimethylsilyl chloride was added over a period of 10 min. Reaction mixture was allowed to attain room temperature slowly and stirred for 12 h. White precipitate was filtered under inert atmosphere and hexane was evaporated under vacuum. Product was distilled as a colorless liquid at 70° C. @ 20 torr. Yield: 9.4 g (70.0%). $^1$HNMR (400.18 MHz, $C_6D_6$) 5.80 (S, 1H), 2.30 (S, 3H), 2.00 (s, 3H), 0.32 (s, 9H) ppm; $^{13}$CNMR (100.64 MHz, $C_6D_6$) 151.97, 146.04, 108.40, 32.54, 23.63, 1.02 ppm.

(4)

BL3

The synthetic preparation, characterization, and properties, according to $^1$HNMR and $^{13}$CNMR demonstrated good purity and high yields. According to the TGA analysis, these molecules were volatile (highest evaporation rate was between 90-137° C.) and thermally stable with residues of ~0%.

Examples

Trimethylsilylamides were tested as blocking layers by treating substrates (Si(H), $SiO_2$ 1K, Si(native oxide)) in vapor phase with BL1 at 350° C. ALD of SiN at the same temperature was then performed. The silicon precursor used was silicon tetrabromide and the nitrogen-containing precursor comprised ammonia (30 T). There were a total of 100 cycles. Table 1 shows the results from a 2.4 Torr soak of differing lengths with BL1. Table 2 shows the results of a 5 Torr soak for 30 seconds.

TABLE 1

| Soak Time | Film Thickness (Å) | | |
|---|---|---|---|
| (min) | Si(H) | Si(native O) | $SiO_2$ 1K |
| 30 | 30.4 | 4.58 | 2.65 |
| 10 | 28.4 | 2.02 | 2.18 |
| 5 | 31.7 | 4.98 | 2.12 |
| 1 | 32.5 | 5.2 | 2.59 |
| 0.5 | 31.33 | 7.19 | 2.62 |
| 0 | 28.5 | 28.23 | 20.39 |

TABLE 2

| Soak Time | Film Thickness (Å) | | |
|---|---|---|---|
| (min) | Si(H) | Si(native O) | $SiO_2$ 1K |
| 0.5 | 25.3 | 1.1 | 0.84 |

When BL1 was not used as a pretreatment, there was very little observed selectivity with respect to Si(H), $SiO_2$ 1K and Si(native O). BL1 Soak times of greater than 1 minute at 2 T enabled very good selectivity. According to contact angle measurements, there was little or no SiN deposited on the $SiO_2$ and Si(native O) substrates. This was verified by the hydrophillicity on Si(H) vs. hydrophobicity on $SiO_2$ and Si(native O). At 30 seconds of BL1 soak time, there was still some selectivity based on Ellipsometry, however, the contact angles were very similar, which might suggest that there is SiN on all three surfaces. Increasing the pressure to 5 T for 30 seconds recovered the selectivity.

The selectivity of BL1 as a function of the number of cycles was also evaluated. The results are collected in Table 3. After 100 cycles, a selectivity of ~8.6 (Si(H) vs $SiO_2$) was observed. After 100 cycles the selectivity appeared to decrease. Without being bound by any particular theory of operation, it is believed that the BL1 blocking layer promotes a nucleation delay which lasts about 100 cycles.

TABLE 3

| Number of | Film Thickness (Å) | | |
|---|---|---|---|
| ALD cycles | Si(H) | Si(native O) | $SiO_2$ 1K |
| 50 | 13 | 1 | 1 |
| 100 | 29 | 5 | 3 |
| 150 | 47 | 25 | 17 |
| 200 | 111 | 86 | 82 |

While the foregoing is directed to embodiments of the present disclosure, other and further embodiments of the disclosure may be devised without departing from the basic scope thereof, and the scope thereof is determined by the claims that follow.

What is claimed is:
1. A method of depositing a film, the method comprising:
   exposing a substrate to a silylamide to react with a hydroxyl-terminated first substrate surface to form a silyl ether-terminated surface, the substrate having a hydrogen-terminated second substrate surface, one or more of the first surface and the second surface comprising a dielectric; and
   forming a film on the second surface selectively over the first surface by exposing the substrate to one or more deposition gases.

2. The method of claim 1, wherein the silylamide comprises an organic silylamide.

3. The method of claim 2, wherein the organic silylamide comprises a silicon atom bonded to substantially only to carbon and/or nitrogen atoms.

4. The method of claim 2, wherein the organic silylamide comprises substantially no Si—H or Si—OH bonds.

5. The method of claim 2, wherein the organic silylamide comprises one or more of trimethylsilylamide, triethylsilylamide, ethyldimethylsilylamide and/or diethylmethylsilylamide.

6. The method of claim 1, wherein the silylamide includes an amide comprising one or more of pyrrolidine, pyrrole, pyrazole, dimethylamine, diethylamine, ethylmethylamine, cyclic secondary amine, saturated cyclic amine and/or unsaturated cyclic amine.

7. The method of claim 1, wherein the silylamide comprises one or more of 1-trimethylsilylpyrrolidine, 1-trimethylsilylpyrrole and/or 3,5-dimethyl-1-trimethylsilylpyrazole.

8. The method of claim 1, wherein the first substrate surface comprises a dielectric.

9. The method of claim 1, further comprising etching the silyl ether-terminated surface after a predetermined amount of film is formed on the second surface followed by re-exposure to the silylamide to re-form the silyl ether-terminated surface and additional film formation.

10. The method of claim 9, wherein the silyl ether-terminated surface is etched and re-formed after no more than 300 atomic layer deposition cycles.

11. The method of claim 1, wherein the substrate is exposed to the silylamide for a time in the range of about 10 seconds to about 60 minutes.

12. The method of claim 1, wherein the film comprises SiN.

13. The method of claim 12, wherein the film is deposited by atomic layer deposition comprising sequential exposure to a silicon-containing gas and a nitrogen-containing gas.

14. The method of claim 13, wherein the silicon containing gas comprises one or more of silane, disilane, trisilane, monochlorosilane, dichlorosilane, trichlorosilane, silicon tetrachloride, hexachlorodisilane (HCDS), a halogenated carbosilane.

15. The method of claim 13, wherein the nitrogen-containing gas comprises one or more of a nitrogen-containing plasma, ammonia, an amine, hydrazine and/or carbonitride.

16. A method of depositing a film, the method comprising:
providing a substrate comprising a first substrate surface having a hydroxyl-terminated surface and a second substrate surface having a hydrogen-terminated surface, one or more of the first substrate surface and the second substrate surface comprising a dielectric;
reacting the hydroxyl-terminated surface of the first substrate surface with a silylamide soak to form a silyl ether-terminated surface; and
depositing a silicon nitride film selectively on the second substrate surface over the first substrate surface by an atomic layer deposition process in which the substrate is sequentially exposed to a silicon containing gas and a nitrogen-containing gas.

17. The method of claim 16, wherein the silylamide comprises silicon atoms bonded to substantially only to carbon and/or nitrogen atoms and there are substantially no Si—H or Si—OH bonds, and the silylamide includes an amide comprising one or more of pyrrolidine, pyrrole, pyrazole, dimethylamine, diethylamine, ethylmethylamine, cyclic secondary amine, saturated cyclic amine and/or unsaturated cyclic amine.

18. The method of claim 17, wherein the silylamide comprises one or more of 1-trimethylsilylpyrrolidine, 1-trimethylsilylpyrrole and/or 3,5-dimethyl-1-trimethylsilylpyrazole.

19. The method of claim 18, wherein the silicon containing gas comprises one or more of silane, disilane, trisilane, monochlorosilane, dichlorosilane, trichlorosilane, silicon tetrachloride, hexachlorodisilane (HCDS) or a halogenated carbosilane and the nitrogen-containing gas comprises one or more of a nitrogen-containing plasma, ammonia, an amine, hydrazine or carbonitride.

20. A method of depositing a film, the method comprising:
providing a substrate comprising a first substrate surface including a hydroxyl-terminated surface and a second substrate surface including a hydrogen-terminated surface, one or more of the first substrate surface and the second substrate surface comprising a dielectric;
soaking a substrate comprising a hydroxyl-terminated first substrate surface and a hydrogen-terminated second substrate surface with a silylamide to react with the hydroxyl-terminated first substrate surface to form a silyl ether-terminated substrate surface, the silylamide comprising one or more of 1-trimethylsilylpyrrolidine, 1-trimethylsilylpyrrole or 3,5-dimethyl-1-trimethylsilylpyrazole; and
forming a silicon nitride film on the second substrate surface selectively over the first substrate surface by sequentially exposing the substrate to a silicon containing gas in a first process region, laterally move the substrate through a gas curtain to a second process region and expose the substrate to a nitrogen-containing gas in the second process region.

* * * * *